US008835505B1

(12) United States Patent
Owoo et al.

(10) Patent No.: US 8,835,505 B1
(45) Date of Patent: *Sep. 16, 2014

(54) READY-TO-USE CO-SOLVENTS PHARMACEUTICAL COMPOSITION IN MODIFIED FLEXIBLE PLASTIC CONTAINER

(71) Applicants: Welgrace Research Group, Lindenhurst, IL (US); HQ Specialty Pharma Corporation, Paramus, NJ (US)

(72) Inventors: George Owoo, Lindenhurst, IL (US); Erica Castagna, Tirano (IT)

(73) Assignees: Welgrace Research Group, Lindenhurst, IL (US); HQ Specialty Pharma Corporation, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/840,153

(22) Filed: Mar. 15, 2013

(51) Int. Cl.
*A61K 31/045* (2006.01)
*A61K 31/047* (2006.01)
*A61K 31/24* (2006.01)
*A61K 31/138* (2006.01)
*A61K 31/215* (2006.01)
*A61K 47/10* (2006.01)
*A61K 31/216* (2006.01)
*B65B 55/02* (2006.01)

(52) U.S. Cl.
CPC ............. *B65B 55/02* (2013.01); *A61K 31/216* (2013.01)
USPC ......................................... 514/652

(58) Field of Classification Search
None
See application file for complete search history.

(56) References Cited

U.S. PATENT DOCUMENTS

| 4,707,389 A | * | 11/1987 | Ward ........................... 428/36.6 |
| 4,857,552 A | * | 8/1989 | Rosenberg et al. ........... 514/538 |
| 6,528,540 B2 | * | 3/2003 | Liu et al. ...................... 514/538 |
| 7,527,619 B2 | * | 5/2009 | Domkowski et al. ......... 604/415 |
| 2008/0292558 A1 | * | 11/2008 | Tiwari et al. ................. 424/10.3 |

FOREIGN PATENT DOCUMENTS

WO    WO02/076446 A1    10/2002

OTHER PUBLICATIONS

Ghostine et al. (European Heart Journal 2008, 29, 2133-2144.*
International Search Report and Written Opinion issued May 29, 2014 in PCT/US14/27992.

* cited by examiner

*Primary Examiner* — Ernst V Arnold
(74) *Attorney, Agent, or Firm* — Oblon, Spivak, McClelland, Maier & Neustadt, L.L.P.

(57) ABSTRACT

A ready-to-use injectable, co-solvents (ternary mixture) pharmaceutical composition for the treatment of cardiac conditions and diagnosis applications, comprising methyl-3-[4-(2-hydroxy-3-isopropylamino)propoxy]phenylpropionate hydrochloride (Esmolol hydrochloride), a buffering agent, ethanol and propylene glycol. The ready-to-use injectable, co-solvents (ternary mixture) pharmaceutical composition is capable of being stored in a modified flexible plastic container that may be heat-sterilized without deformation and/or without having the integrity of the closure system being compromised. A method for the manufacture of the ready-to-use injectable, co-solvents (ternary mixture) pharmaceutical composition is also disclosed.

18 Claims, No Drawings

READY-TO-USE CO-SOLVENTS PHARMACEUTICAL COMPOSITION IN MODIFIED FLEXIBLE PLASTIC CONTAINER

SUMMARY OF THE INVENTION

In general, this invention relates to ready-to-use pharmaceutical compositions of Esmolol, or a pharmaceutically acceptable salt thereof, that are formulated in co-solvents matrix, stored in flexible plastic container subjected to sterilization via moist-heat autoclaving for administration to a patient, without further dilution. Further, the compositions of the formulated as a pharmaceutical composition for treating/administration to a subject for reduction of heart rate during cardiac catheterization (i.e. ablation of atrial fibrillation) and diagnosis of cardiac disease via medical imaging (i.e. coronary computerized tomography).

BACKGROUND OF THE INVENTION

Esmolol, the methods for making and for treatment or prophylaxis of cardiac disorders using such compounds are disclosed in U.S. Pat. Nos. 4,387,103 and 4,593,119, incorporated herein by reference. Esmolol and its pharmaceutically acceptable salts, (e.g., hydrochloride salt) and related compounds have β-adrenergic blocking activity. It is a short-acting β-blocker, used in acute care settings to control the heart rate of a patient.

Esmolol is approved treating high blood pressure or rapid heart rate that occurs during or after surgery. It is also used in treating very rapid and irregular heart rates in emergency situations in particularly, atrial fibrillation, atrial flutter, or other similar irregular heart rhythms originating in the atria of the heart (the upper chambers). Under certain conditions some healthcare providers have administered Esmolol and other beta-blockers medication and/or prescribe as "off-label" uses for several coronary-imaging techniques including diagnosis of cardiac disease via medical imaging. The use of beta-blockers to reduce the heart rate that greatly influences and/or improves image quality and stenosis detection is well described (see for example, Ropers D et al. (2006) "Usefulness of multidetector row spiral computed tomography with 64×0.6-mm collimation and 330-ms rotation for the noninvasive detection of significant coronary artery stenoses". Mollet N R et. al., "Multislice spiral computed tomography coronary angiography in patients with stable angina pectoris". J Am Coll Cardiol (2004) 43:2265-2270, Nikolaou K et al. "Accuracy of 64-MDCT in the diagnosis of ischemic heart disease" (2006), Pugliese F et al. "Diagnostic accuracy of non-invasive 64-slice CT coronary angiography in patients with stable angina pectoris. Eur Radiol 16:575-582 Raff G L, Goldstein J. A. et. al. "Coronary angiography by computed tomography: coronary imaging evolves". J Am Coll Cardiol. 2007 May 8; 49(18):1830-); and other references. The current clinical practice for reducing or inducing lower heart rate to enable coronary computed tomography, quality coronary images is to prescribe long acting beta-blockers, oral medication of either Metroprolol or Atenolol of about 50-100 mg for several hour prior to the schedule procedures. Although, eventually the target heart rate of between 50 to 60 beat per minutes would be achieved by multiple combination of tablets and bolus injection of long acting beta-blockers, there are more drawbacks. Since most of these off-label uses are not based well designed clinical studies, the formulation, dosing regimen are also not designed to provided the optimal safety and effectiveness during such procedures. Current Esmolol premixed (vial and bag) presentations are not suitable for several coronary-imaging techniques due to the drawbacks of the formulation strength and dosing regimen of about 400 microgram per kilogram per minute which would maintain a heart rate of between 50 to 60 beat per minute for short procedures lasting between 0.5-1 hour) without heart fluctuation.

Esmolol hydrochloride{methyl3-[4-[2-hydroxy-3-(isopropylamino) propoxy]phenyl]propionate hydrochloride} is a water soluble molecule but would chemically decomposed via an acid/base catalyzed hydrolysis. The decomposition of Esmolol in aqueous environment is sole due to the labile aliphatic methyl ester group, that degrades into Esmolol acid free (also known as ASL-8123) {methyl3-[4-[2-hydroxy-3-(isopropylamino) propoxy]phenyl]propionic acid} and methanol. However, in some organic solvents and/or mixtures thereof, the rate of decomposition of Esmolol can be reduced, which was first disclosed in U.S. Pat. No. 5,017,609 and U.S. App. No. 20080293810. The concept of Premixed or Ready-to-use for Esmolol was first prepared for a concentrate from Brevibloc® 250 mg/mL, 10-mL ampoule presentation by Baaske, al. et., (see Baaske, D M. "Stability of esmolol hydrochloride in intravenous solutions." Amer J of Hosp Pharmacy 51.21 (1994) pp 2693-6). The stability of admixture solutions of Esmolol Injection was limited to a few days in a PVC infusion bags. Escobar et. al., and Tiawari et. al., (see U.S. Pat. No. 5,017,609 and U.S. App. No. 20080293810) suggested that organic solvents have the ability of reducing the rate of degradation of Esmolol in co-solvent matrix. In 2007, Brevibloc® (Esmolol HCl) Injection, 250 mg/mL, 10-mL ampoule was withdrawn for the USA due solely to serious adverse events via medication errors. However, the chemical stability of Esmolol HCl and it compatibility to containers has proven to be very challenging for commercial viability due to its rapid decomposition in solutions. Several formulations of Esmolol HCl have been studied, with the degradation profile and the stability well characterized. However, the ability to aseptically, terminally sterilize by moist heat sterilization and/or other forms of sterilization of drugs in flexible plastic containers is still a "black box" especially co-solvent formulations with multiple instabilities and sterility issues.

Brevibloc® (Esmolol HCl) Injection, ready-to-use non-isotonic and isotonic formulations of Esmolol are disclosed in (U.S. Pat. Nos. 4,857,552, 6,310,094, 6,528,540, and U.S. App. No. 20080293814, 20100311738, Baaske, D M. "Stability of esmolol hydrochloride in intravenous solutions." Amer J of Hosp Pharmacy 51.21 (1994): 2693-6, Rosenberg, L. S. et. al., "An accurate Prediction of the pH Change Due to Degradation: Correction for a "Produced" Secondary Buffering System." Pharmaceutical Research_5.8 (1988): 514-517) packaged in either vial or plastic containers, respectively, incorporated herein by reference. In the prior art of the above mentioned references, the formulations of Esmolol in totally aqueous environment were stabilized via pH and self-buffering of the ASL-8123 {methyl3-[4-[2-hydroxy-3-(isopropylamino) propoxy]phenyl]propionic acid}. The rate of degradation of Esmolol hydrochloride in totally aqueous formulation is minimized by the concentration of Esmolol, buffer/self-buffering molecules within a near pH range. These formulations maintain a reasonable shelf-life, however, upon terminal sterilization in either in glass vials or flexible plastic, degradation occurs. As a result, prior art formulation package in vial (small volume parenteral) is prepared aseptically while the flexible plastic container (large volume parenteral) is terminally sterilized.

Currently, the commercialized products of Esmolol in the marketplace are these ready-to-use isotonic formulations in both flexible plastic and vial presentations. Lui et. al, taught that the ready-to-use isotonic formulations in containers were could be terminally sterilized, with significant decomposition. Further, larger volume parenteral injections are stored in IntraVia™ flexible plastic, a semi-free of PVC, such as those disclosed in U.S. Pat. Nos. 5,849,843 and 5,998,019 and are typically prefer by the national intravenous therapy association and regulatory authorities for being terminal sterilized. Terminal sterilization as a way of reducing microbiological burden and ensure patient safety of the finished product. However, not all drug formulations, and containers can withstand this technique of sterilization.

It is well known, described and documented in the pharmaceutical industry and any one skilled in the art of formulating co-solvent matrixes in medical plastics (flexible container or multi-layer plastic bags) are not compatible for long-storage due to multi-dimensional safety concerns. To name are few potential drawbacks; soften of the polymers, swallowing/collapse film materials, potential leachable (both drug and inks), drug incompatibility and deformation of the container closure system. Furthermore, for large volumes parenteral that require stricter microbiological controls and limits not to exacerbate cross-contaminations to already compromised patients, terminal sterilization is required. Multiple formulations of co-solvents, lipids, exotic encapsulations ranging from small molecules, large, lipophilic, hydrophobic, insoluble molecules, complex formulation with surface reducing agents, unstable drug substances, etc., have been stored for in medical plastic containers for small volume parenteral with major challenges. The exceptions to aforementioned are foods and cosmetics formulation that may not be suitable for injection and/or systemic circulation (drug delivery). An Intralipid formulation in flexible containers is worth noting, where perhaps different polymeric materials and process are used to claim sterility and non-cross microbiological contamination.

Liu et al. in U.S. Pat. Nos. 6,310,094 and 6,528,540 teach a heat sterilized esmolol formulation packaged in PVC bags. The patents all rely on the absence of ethanol and propylene glycol for success. Previous ready to use formulations had used both ethanol and propylene glycol as esmolol solubilizers. Prior formulations using these alcohols could not be successfully heat sterilized.

For over thirty years, Polyvinyl Chloride (PVC) flexible container and its shortcomings has been the commercial choose and the rate-limiting step for development of premixes in large volume parenteral injection. In recent past, the introduction of new flexible plastic container has improved, and issues of water loss, higher levels of extractables and port closure system integrity testing have been resolved. New flexible container material system and suitable port closures have be designed and more particularly, flexible autoclavable intravenous (IV) containers or bags of non-PVC polyolefin film (e.g., polyethylene or polypropylene) (polymeric materials are disclosed in U.S. Pat. Nos. 4,654,240, 5,849,843, 5,783,269, 5,998,019, 6,255,396, 6,461,696, and 6,590,033) nylon, or a composite material, either laminated or co-extruded structure (including both monolayer and multilayer structures). It is also possible to utilize bags composed of laminates where the inner laminate is inert to the solution such a bags with a polyolefin or polyethylene vinyl acetate (EVA). Non-PVC flexible plastic containers are considered to be relatively inert and contain low levels of extractable materials when subjected to aqueous or non-lipophillic drug substance/products. However, impart of co-solvents formulation, softness and deforms non-PVC films, leaching from the film and the heat sealed ports and closures becomes unacceptable for storage of certain pharmaceuticals. The non-PVC plastic films provides long shelf life for IV fluid containers, due to low moisture vapor transmission rate, and low levels extractables terminal sterilization using high temperature treatment, i.e., sterilized after filling to deactivate microorganisms inside the containers (e.g., autoclaving) are not suitable for all pharmaceutical formulations. Though, these new materials and technologies offered the pharmaceutical industry some flexibility in totally aqueous medias/formulations, additional US or European regulatory requirements on autoclave temperature, accumulative extractables for laminated or multilayer materials, administrative, injection ports and closure tips (systems) (polymeric materials/ports are disclosed in U.S. Pat. Nos. 4,778,697, 5,976,300, 5,590,777, 6,869,653 and 7,207,157) have made it desirable for some pharmaceutical premixed to be designed in containers with lower moisture vapor transmission rate without the need for overwraps each container. The challenges facing premixed formulations are the long-term stability, the functionality of the complete assembled container/bag, and non-predicable adsorption and desorption for the longer term. All prior art for most of commercial flexible plastic container/bag has been focused totally aqueous formulations, while co-solvents, surfactants formulation or proteins are limited.

It is well known, characterized and well documented in literature and several patents that commercially available flexible plastic containers, both PVC, non-PVC plastic films are not compatible with certain drug substances due to their innate properties. Jenke, D. R. et. al., "Evaluation of model solvent systems for assessing the accumulation of container extractables in drug formulations" Int. J. Pharm. 224, 51-60; "Use of binary ethanol/water model solutions to mimic the interaction between a plastic material and pharmaceutical formulations" J. Appl. Polym. Sci. 89, 1049-1057; Thiesen, J. et. al. "physico-chemical stability of docetaxel premix solution and doxcetaxel infusion in PVC and polyolefine containers" Journal of Pharmacy World & Science, vol. 21, #3, June 1999, pp 137-141; Trissel L. A. et. al. "Handbook on Injectables drugs, 15th edition, Bethesda, Md.: American Society of Health-System Pharmacists, 2009; Moorhatch, P. et. al., "Interaction between drugs and plastic intravenous fluid bags. I sorption studies on 17 drugs." Am. J. Hosp. Pharm. 31, 72-78; have used both PVC, non-PVC plastic films, and other plastic elastomers to show that there is a non-specific adsorption/desorption of drugs and drug matrixes from flexible plastic containers. Thus, formulations of drug substances in conjunction with drug matrixes such co-solvents and/or surfactants are not stable and they stability cannot be predicted in commercially available flexible plastic containers. Further, when these flexible plastic containers are stressed with delivery devices (i.e. sterilization via moist-heat processes), significant decomposition of the drug, deformity and leachables of the flexible plastic containers are detected.

DETAILED DESCRIPTION OF THE INVENTION

It is an object of the present invention to provide a co-solvent sterile premixed pharmaceutical product of esmolol hydrochloride injectable for the treatment of treatment of cardiac conditions, reducing heart rate during medical procedures, managing acute atrial fibrillation to prevent ischemic stroke and improving the quality of diagnosis images of coronary computerized tomography.

To this end, the present invention provides a co-solvent sterile premixed pharmaceutical product stored in a non-PVC flexible plastic container, where the pharmaceutical product has a solution pH between 4.5 and 5.5 and contains:

a. 5 to 40 mg/mL methyl-3-[4-(2-hydroxy-3-isopropylamino)propoxy]phenylpropionate hydrochloride (esmolol hydrochloride),
b. a buffering agent to maintain a solution pH between 4.5 and 5.5,
c. 0.1% to 3 w/v % of ethyl alcohol, and
d. 0.1% to 3 w/v % of one of propylene glycol or glycerin; and the pharmaceutical product is contained in a sealed container and heat-moist sterilized (e.g., autoclaved) for a period of time sufficient to render the composition sterile.

Thus, an embodiment of the present invention provides a premixed (Ready-to-use), stable, parenteral co-solvents formulation of Esmolol hydrochloride and a pharmaceutically acceptable salt with concentration ranging from 5-40 mg/mL, buffered with sodium acetate and/or sodium tartrate of 0.05 to 2.3 mg/mL, respectively, containing both ethyl alcohol and propylene glycol ranging from 0.1 to 3% (weight/volume) each, packaged in a non-PVC plastic container with modified ports and container closure systems and which is terminal sterilization at temperature of at least about 110° C. to 130° C. via autoclaving with a dwelling time ranging from 7 to 30 minutes. Esmolol hydrochloride formulated in co-solvents matrix has been shown in prior art cannot survive autoclaving (U.S. Pat. No. 5,017,609 and U.S. App. No. 20080293810). The resultants of terminal sterilization are increased degradation products and other related esters of Esmolol, which have the same or similar pharmacological activities. The present invention is stable Esmolol hydrochloride{methyl3-[4-[2-hydroxy-3-(isopropylamino) propoxy]phenyl]propionate hydrochloride} in co-solvents matrix stored in plastic container that subjected to heat-moist sterilization without physical integrity/deformity ("deformity" is been define/means that the flexible plastic container and closure system failed a dye immersion test in accordance to USP compendia) of the plastic flexibility of the plastic container compromised, and additional essentially free of leachable material. The surprising findings were linked to increased stability Esmolol and the composition ratios at lower co-solvents when subjected to moist-heat sterilization, where the decomposition of the Esmolol after autoclaving range from 0.5 to 2% (Esmolol acid free, also known as ASL-8123). Additionally, formation of the related esters generate via heat induce or proposed transesterification were not present and were at trace levels after 6 months of storage under accelerated condition of 40° C. ("trace levels" means the observed peak were below the limit of detection for the HPLC method used which was 0.03% (weight/weight). The prior art U.S. Pat. No. 5,017,609 and App. No. 20080293810 provided a teaching of composition ratio of ethanol:propylene glycol:Esmolol (1:1:1) with a concentration range of 5-60% by volume ratio and benzyl alcohol, formation of related esters of Esmolol, but did not include any teaching as to how, when or if the product is stored in a flexible plastic container and terminally sterilized. Further, this reference does not teach or guidance effect of the stability at lower co-solvents composition and Esmolol concentrations of the related esters of Esmolol as formulated in a non-glass container(s). Since the pH of an infusion can contribute to phlebitis, then it is critical to control the pH of composition during its shelf life (where acid degradation products affects the solution matrix).

In addition, the present invention provides premixed stable pharmaceutical, parenteral co-solvents formulation of Esmolol hydrochloride and a pharmaceutically acceptable salt at with concentration of 5-40 mg/mL, buffered with sodium tartrate of 0.1 to 1.5 mg/mL, containing both ethyl alcohol and glycerin ranging from 0.1 to 3.0% (weight/volume) each, packaged in a non-PVC plastic container which is terminal sterilization at temperature of at least about 110° C. to 130° C. via autoclaving with a dwelling time ranging from 7 to 30 minutes. This compositions of the formulated as a pharmaceutical composition premixed for continuous infusion in subjects undergoing diagnosis of cardiac disease via medical imaging (i.e. coronary computerized tomography) and/or induce heart rate reduction of during cardiac catheterization such as ablation of atrail fibrillation. A formulation of Esmolol with a strength of 30 mg/mL dose/infused at about 400 microgram per kilogram per minute would maintain and or provide a steady heart rate between 50 to 60 beat per minute for short procedures lasting between 0.5-1 hour) without heart fluctuation. This would improve the images of the coronary computerized tomography and improve the diagnosis of cardiac disease and treatment.

Esmolol hydrochloride formulated in co-solvents matrix has been shown in prior art cannot survive autoclaving (U.S. Pat. No. 5,017,609 and U.S. App. No. 20080293810). The resultants of terminal sterilization are increased degradation products and other related esters of Esmolol, which have the same or similar pharmacological activities. The present invention is stable Esmolol hydrochloride{methyl3-[4-[2-hydroxy-3-(isopropylamino) propoxy]phenyl]propionate hydrochloride} in co-solvents matrix stored in plastic container that subjected to heat-moist sterilization without physical integrity/deformity ("deformity" is been define/means that the flexible plastic container and closure system failed a dye immersion test in accordance to USP compendia) of the plastic flexibility of the plastic container compromised, and additional essentially free of leachable material. The surprising findings were linked to increased stability Esmolol and the composition ratios at lower co-solvents when subjected to moist-heat sterilization, where the decomposition of the Esmolol after autoclaving range from 0.5 to 2% (Esmolol acid free, also known as ASL-8123). Additionally, formation of the related esters generate via heat induce or proposed transesterification were not present and were at trace levels after 6 months of storage under accelerated condition of 40° C. ("trace levels" means the observed peak were below the limit of detection for the HPLC method used which was 0.03% (w/w). The prior art U.S. Pat. No. 5,017,609 and App. No. 20080293810 provided a teaching of composition ratio of ethanol:propylene glycol:Esmolol (1:1:1) with a concentration range of 5-60% by volume ratio and benzyl alcohol, formation of related esters of Esmolol, but did not include any teaching as to how, when or if the product is stored in a flexible plastic container and terminally sterilized. Further, this reference does not tech or guidance effect of the stability at lower co-solvents composition and Esmolol concentrations of the related esters of Esmolol as formulated in a non-glass container(s). Since the pH of an infusion can contribute to phlebitis, then it is critical to control the pH of composition during its shelf life (where acid degradation products affects the solution matrix).

The apparent pH should be between 4.5 and 6.0, or between 4.5 and 5.5, or between 5 and 5.3. Buffering agents are preferably included in the composition to maintain the pH at preferred target between 4.5 and 5.5 over the course of the shelf-life. Suitable buffering agents are known in the art, including acetate, tartrate, malate and furmarate. Preferred buffering agents are sodium acetate and sodium tartrate. The pH can be appropriately adjusted by use of a suitable amount of an appropriate acid or base to achieve the desired pH. Hydrochloric acid is mentioned as a exemplary acid, while sodium hydroxide is mentioned as an exemplary base.

As described herein, esmolol is contained in the ready-to-use composition of the present invention in an amount ranging from 5 to 40 mg/mL. In further embodiments of the present invention, the minimum concentration of esmolol in the ready-to-use composition can be 5 mg/mL, 6 mg/mL, 7 mg/mL, 7.5 mg/mL, 8 mg/mL, 9 mg/mL, 10 mg/mL, 15 mg/mL 20 mg/mL, 25 mg/mL and the maximum concentration of esmolol can be 40 mg/mL, 37.5 mg/mL, 35 mg/mL, 32.5 mg/mL, 30 mg/mL, 27.5 mg/mL, 25 mg/mL, 22.5 mg/mL, 20 mg/mL, 17.5 mg/mL or 15 mg/mL, inclusive of all ranges and sub-ranges embraced therein. Exemplary ranges for the esmolol concentration include 5 to 40 mg/mL, or from 7.5 to 35 mg/mL, 10 to 40 mg/mL, or from 10 to 35 mg/mL, or from 10 to 30 mg/mL, or from 10 to 25 mg/mL, or from 10 to 20 mg/mL, or from 10 to 15 mg/mL.

As described herein, sodium acetate and/or sodium tartrate is contained in the ready-to-use composition of the present invention in an amount ranging from 0.05 to 2.3 mg/mL. In further embodiments of the present invention, the minimum concentration of sodium acetate and/or sodium tartrate can be 0.05 mg/mL, 0.1 mg/mL, 0.15 mg/mL, 0.2 mg/mL, 0.25 mg/mL, 0.3 mg/mL, 0.35 mg/mL, 0.4 mg/mL, 0.45 mg/mL, 0.5 mg/mL, 0.55 mg/mL, 0.60 mg/mL, or 0.65 mg/mL and the maximum concentration of sodium acetate and/or sodium tartrate can be 2.3 mg/mL, 2.25 mg/mL, 2.2 mg/mL, 2.15 mg/mL, 2.1 mg/mL, 2.05 mg/mL, 2.0 mg/mL, 1.95 mg/mL, 1.90 mg/mL, 1.85 mg/mL, or 1.8 mg/mL, inclusive of all ranges and sub-ranges embraced therein. Exemplary ranges for the sodium acetate and/or sodium tartrate concentration include from 0.05 to 2.3 mg/mL, or from 0.1 to 2.3 mg/mL, or from 0.2 to 2.3 mg/mL, or from 0.3 to 2.3 mg/mL, or from 0.4 to 2.3 mg/mL, or from 0.5 to 2.3 mg/mL, or from 0.6 to 2.2 mg/mL, or from 0.65 to 2.1 mg/mL or from 0.65 to 2.0 mg/mL, or from 0.65 to 1.9 mg/mL or from 0.65 to 1.8 mg/mL.

As described herein, the ready-to-use composition may further contain glacial acetic acid. When present, the glacial acetic acid may be contained in an amount ranging from 0.002 to 0.4 mg/mL. In further embodiments of the present invention, the minimum concentration of glacial acetic acid can be 0.002 mg/mL, 0.0025 mg/mL, 0.003 mg/mL, 0.0035 mg/mL, 0.004 mg/mL, 0.0045 mg/mL, or 0.005 mg/mL and the maximum concentration of glacial acetic acid can be 0.4 mg/mL, 0.375 mg/mL, 0.35 mg/mL, 0.325 mg/mL, 0.3 mg/mL, 0.275 mg/mL, or 0.25 mg/mL, inclusive of all ranges and sub-ranges embraced therein. Exemplary ranges for glacial acetic acid concentration, when present, include from 0.002 to 0.4 mg/mL, or from 0.0025 to 0.35 mg/mL, or from 0.003 to 0.3 mg/mL.

As described herein, the ready-to-use composition may further contain tartaric acid. When present, the tartaric acid may be contained in an amount ranging from 0.005 to 0.9 mg/mL. In further embodiments of the present invention, the minimum concentration of tartaric acid can be 0.005 mg/mL, 0.01 mg/mL, 0.015 mg/mL, 0.02 mg/mL, 0.025 mg/mL, 0.03 mg/mL, or 0.035 mg/mL and the maximum concentration of tartaric acid can be 0.9 mg/mL, 0.85 mg/mL, 0.8 mg/mL, 0.75 mg/mL, 0.7 mg/mL, 0.65 mg/mL, or 0.6 mg/mL, inclusive of all ranges and sub-ranges embraced therein. Exemplary ranges for tartaric acid concentration, when present, include from 0.005 to 0.9 mg/mL, or from 0.015 to 0.85 mg/mL, or from 0.02 to 0.8 mg/mL, or from 0.25 to 0.75 mg/mL.

As described herein, ethyl alcohol (i.e., ethanol) is contained in the ready-to-use composition of the present invention in an amount ranging from 0.1 to 3% (all percentages herein under are weight/volume). In further embodiments of the present invention, the minimum concentration of ethyl alcohol can be 0.1%, 0.15%, 0.2%, 0.25%, 0.3%, 0.35%, 0.4%, 0.45%, or 0.5% and the maximum concentration of ethyl alcohol is 3%, 2.75%, 2.5%, 2.25%, 2%, 1.75%, 1.5%, 1.25%, 1%, 0.75%, or 0.5%, inclusive of all ranges and sub-ranges embraced therein. Exemplary ranges for the ethyl alcohol concentration include from 0.1 to 3%, or from 0.1 to 2.5%, or from 0.1 to 2%, or from 0.1 to 1.5%, or from 0.1 to 1%, or from 0.1 to 0.5%, or from 0.15 to 3%, or from 0.15 to 2.5%, or from 0.15 to 2%, or from 0.15 to 1.5%, or from 0.15 to 1%, or from 0.15 to 0.5%.

Where propylene glycol is contained in the ready-to-use composition of the present invention it is present in an amount ranging from 0.1 to 3% (all percentages herein under are weight/volume). In further embodiments of the present invention, the minimum concentration of propylene glycol can be 0.1%, 0.15%, 0.2%, 0.25%, 0.3%, 0.35%, 0.4%, 0.45%, or 0.5% and the maximum concentration of ethyl alcohol is 3%, 2.75%, 2.5%, 2.25%, 2%, 1.75%, 1.5%, 1.25%, 1%, 0.75%, or 0.5%, inclusive of all ranges and sub-ranges embraced therein. Exemplary ranges for the propylene glycol concentration include from 0.1 to 3%, or from 0.1 to 2.5%, or from 0.1 to 2%, or from 0.1 to 1.5%, or from 0.1 to 1%, or from 0.1 to 0.5%, or from 0.15 to 3%, or from 0.15 to 2.5%, or from 0.15 to 2%, or from 0.15 to 1.5%, or from 0.15 to 1%, or from 0.15 to 0.5%.

In yet another alternative invention, provides a rigid plastic container (vial and bottle configuration) with teflon coated rubber stoppers can be used as closure system suitable for storing premixed solution of Esmolol Injection with co-solvents matrix which is subjected to typically product sterilization by steam sterilization autoclaving, 121° C. for a about 15 minutes) without altering the thermal properties vial and/or bottle, and maintaining the integrity container. The primary polymeric container was made-up of Cryovac's™ M312A film of multiple-layers of at least 5 poly, but the ports and closure system were modified to provide resistance to polymer softening, a moisture barrier, lower leachables and functionality closure system during the stability phase and shelf life of the formulation ("functionality" of the closure system is been define as the spiking of the closure system to enable flow using an infusion sets). The modifications to flexible plastic container ports and closure system were necessary due the drawbacks observed when co-solvent formulations of Esmolol were stress commercially available flexible plastic containers (bags). These drawbacks of the unmodified bags were failure of container closure integrity in accordance with USP dye immersion, higher levels of leachables, and collapse of port access for an IV spike (infusion set spike) to puncture membrane. The ports and the closure system preferably uses commercially available polymers, elastomers etc., the administrative and additive ports were made off external coextruded layer consists of synthetic thermoplastic rubber (Raumedic SRT320) ranging from about 20 to 30% based on an elastomer modified polypropylene. While the internal coextruded layer (PE770) of not more than 50% in composition consists of ethylenvinyl acetate without any further additives (EVA). The tubing ports are made of two-layer materials, which can withstand both terminal sterilization and co-solvent matrix. Furthermore, the twist-off compositions were made of polyproplene Granuflex® 4489 between 70-80% and Granuflex® 4371 15-20%. However, other polymers stable, low leachables, and without physical deformation as defined previously in the presence of the esmolol solution and to heat sterilization may also be used for the ports and closure assemblies, referred to as modified ports and closures.

Commercially available flexible plastic containers (bags) such as Excel® (Braun Company), Visiv® (Hospira), Necexl® (Sealed Air), Intervia® (Baxter), Technoflex, etc., for pharmaceutical formulation or medical liquids are assemble of different plastic materials of different properties, thermal resistance and functionalities. They are typically designed and tested mostly for aqueous formulations admixtures, premixed or ready-to-use pharmaceutical products. Still the combination of the co-solvents and drug composition subjected to further heat sterilization can adversely effect, plastic materials, sealing integrity and the solutions contained therein unless they are maintained at certain conditions.

In another alternative invention, provides a flexible plastic container with modified ports and closure system suitable for storing premixed solution of Esmolol Injection with co-solvents matrix which is subjected to typically product sterilization by steam sterilization (autoclaving, 121° C. for a about 15 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. The premixed stable pharmaceutical, parenteral co-solvents formulation of Esmolol hydrochloride and a pharmaceutically acceptable salt at with concentration of 5-40 mg/mL, buffered with sodium tartrate of 0.1 to 1.5 mg/mL, containing both ethyl alcohol and glycerin ranging from 0.1 to 3.0% (weight/volume) each, packaged in a non-PVC plastic container with modified ports and container closure systems and which is terminal sterilization at temperature of at least about 110° C. to 130° C. via autoclaving with a dwelling time ranging from 7 to 30 minutes.

Where glycerin is contained in the ready-to-use composition of the present invention it is present in an amount ranging from 0.1 to 3% (all percentages herein under are weight/volume). In further embodiments of the present invention, the minimum concentration of glycerin can be 0.1%, 0.15%, 0.2%, 0.25%, 0.3%, 0.35%, 0.4%, 0.45%, or 0.5% and the maximum concentration of glycerin is 3%, 2.75%, 2.5%, 2.25%, 2%, 1.75%, 1.5%, 1.25%, 1%, 0.75%, or 0.5%, inclusive of all ranges and sub-ranges embraced therein. Exemplary ranges for the glycerin concentration include from 0.1 to 3%, or from 0.1 to 2.5%, or from 0.1 to 2%, or from 0.1 to 1.5%, or from 0.1 to 1%, or from 0.1 to 0.5%, or from 0.15 to 3%, or from 0.15 to 2.5%, or from 0.15 to 2%, or from 0.15 to 1.5%, or from 0.15 to 1%, or from 0.15 to 0.5%.

Exemplary embodiments of the formulation of the present invention include:
  A formulation for 10 mg/mL esmolol (2.5 g/250 mL) containing 1% esmolol (10 mg/mL) plus 1% ethyl alcohol (~10 mg/mL) plus 1% propylene glycol (~10 mg/mL) in sodium acetate buffer.
  A formulation for 20 mg/mL esmolol (2.0 g/100 mL) containing 2% esmolol (20 mg/mL) plus 0.5% ethyl alcohol (~5 mg/mL) plus 0.5% propylene glycol (~5 mg/mL) in sodium acetate buffer.
  A formulation for 30 mg/mL esmolol (1.5 g/50 mL) containing 3% esmolol (30 mg/mL) plus 0.1% ethyl alcohol (~1 mg/mL) plus 0.2% glycerin (~2 mg/mL) in sodium tartrate buffer.

An advantage of the present invention is that, unlike prior art compositions of Esmolol, the formulation does not form degredants of other related esters of Esmolol.

A further advantage of the present invention to provide a method of reducing pharmaceutical active substance wastage in formulation of Esmolol usage, which method comprises of titrating to the desire effect wherein the composition requires no dilution prior to administration.

Another advantage of the present invention is that it offers the flexibility and use for the treating/administration to a subject for reduction of heart rate during cardiac catheterization (i.e. ablation of atrial fibrillation) and improved the quality of diagnosis of cardiac disease via medical imaging (i.e. coronary computerized tomography).

Still another advantage of the present invention is that it provides sterile, read-to infused Esmolol compositions that contain less excipients and are simpler for the formulation strength and dosing regimen to be infused at about 200-400 microgram per kilogram per minute which maintains a heart rate of between 50 to 60 beat per minute for short procedures lasting between 0.5-1 hour, without heart fluctuation.

In addition, the flexible plastic container with the modified administrative and injection ports with closure system used for packaging the ready-to-use premix Esmolol have extremely low levels of extractable and leachable materials and thus a safer product during the shelf life of the product.

The present invention also provides a method of controlling bradycardia and/or controlling hypotension in the diagnosis of cardiac conditions using computerized cardiac tomography in humans comprising administering to a subject in need thereof an effective amount of the pharmaceutical product described herein above.

The dosing and route of administration can be readily ascertained by the clinical physician. It is contemplated that the effective amount and administration route of a composition will depend on a number of factors, including by not limited to the age of the patient, immune status, race, and sex of the patient, and the severity of the condition/disease, and the past medical history of the patient, and always lies within the sound discretion of the administering physician.

By way of example only, the following exemplary administration embodiments are provided:
  For the control of high heart rate and hypertension, administration is preferably intravenous using a peripheral and/or central venous access, with a loading dose of 0.5 milligrams/kg infused over 1 minute period of time, for a 70 kg patient, followed by a maintenance infusion rate of 50 mcg/kg/min to the desired therapeutic effect.
  For controlled bradycardia, the administration is preferably intravenous using a peripheral and/or central venous access, with a loading dose of 1 milligrams/kg infused over 1 minute period of time, for a 70 kg patient, followed by a maintenance infusion rate of 200 mcg/kg/min to the desired therapeutic effect.

The present invention further provides methods of preparing the pharmaceutical product described herein above.

One embodiment of the method of preparing the pharmaceutical product, entails:
  preparing a composition comprising:
    a. 5 to 40 mg/mL methyl-3-[4-(2-hydroxy-3-isopropylamino)propoxy]phenylpropionate hydrochloride (esmolol hydrochloride),
    b. a buffering agent to maintain a solution pH between 4.5 and 5.5,
    c. 0.1% to 3 w/v % of ethyl alcohol and
    d. 0.1% to 3 w/v % of one of propylene glycol or glycerin;
  adding the composition to a non-PVC flexible plastic container as defined above; sealing the container; and
  subjecting the sealed container to heat-moist sterilization for a period of time sufficient to render the composition sterile thereby forming said pharmaceutical product.

Another embodiment of the method of preparing the pharmaceutical product, entails:

preparing in a non-PVC flexible plastic container as defined above a composition comprising:
 a. 5 to 40 mg/mL methyl-3-[4-(2-hydroxy-3-isopropylamino)propoxy]phenylpropionate hydrochloride (esmolol hydrochloride),
 b. a buffering agent to maintain a solution pH between 4.5 and 5.5,
 c. 0.1% to 3 w/v % of ethyl alcohol, and
 d. 0.1% to 3 w/v % of one of propylene glycol or glycerin;
sealing said container; and
subjecting the sealed container to heat-moist sterilization for a period of time sufficient to render the composition sterile thereby forming said pharmaceutical product.

Within these embodiments, it is preferred that heat-moist sterilization is autoclaving.

Within these embodiments, it is preferred that the autoclaving temperature range from 110 to 130° C. The autoclaving temperature can be at a minimum temperature of 111° C., 112° C., 113° C., 114° C., 115° C., 116° C., 117° C., 118° C., 119° C., or 120° C. and the maximum temperature can be 130° C., 129° C., 128° C., 127° C., 126° C., 125° C., 124° C., 123° C., 122° C., 121° C., or 120° C., inclusive of all ranges and sub-ranges embraced therein. Exemplary ranges for the autoclaving temperature include from 110 to 130° C., or from 115 to 125° C.

Within these embodiments, it is preferred that the autoclaving time range from 7 to 60 minutes. The autoclaving time can be at a minimum of 7 minutes, 9 minutes, 11 minutes, 13 minutes or 15 minutes and the maximum autoclaving time can be 60 minutes, 45 minutes 30 minutes, 28 minutes, 26 minutes, 25 minutes, 24 minutes, 22 minutes, or 20 minutes, inclusive of all ranges and sub-ranges embraced therein. Exemplary ranges for the autoclaving time include from 7 to 60 minutes, or from 8 to 45 minutes, or from 9 to 30 minutes, or from 10 to 25 minutes, or from 15 to 20 minutes.

The terms "premix" or "premixture" as used herein refers to a pharmaceutical formulation that does not require reconstitution or dilution prior to administration to a patient. For example, in contrast to non-premixed formulations of esmolol, the premixed compositions provided herein are suitable for administration to a patient without dilution by, for example, a clinician, hospital personnel, caretaker, patient or any other individual.

In certain embodiments, the compositions of the present invention can be formulated as "ready to use" compositions which refer to premixed compositions that are suitable for administration to a patient without dilution. For example, in certain embodiments, the compositions of the present invention are "ready to use" upon removing the compositions from a sealed container or vessel.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

The following example compositions and method of manufacture of Esmolol ready-to-use (premixed) containing 5-40 mg/mL of Esmolol HCl, ethanol, propylene glycol and/or glycerin have been provided to further illustrate the invention, but should not be construed as limiting its scope.

Example 1

| Ingredient | Concentration, mg/mL |
|---|---|
| Esmolol | 10-30 mg/mL |
| Sodium Acetate Trihydrate | 0.68-2.04 mg/mL |
| Glacial Acetic Acid | 0.0026 mg/mL |
| Ethyl Alcohol, USP | 0.15-1.5% |
| Propylene glycol USP | 0.15-1.5% |
| Water for Injection, USP | Qs |
| Target pH | 5.2 |

Charge the formulation tank with about eighty percent (80%) of the final volume Water for Injection while sparging with nitrogen (dissolved oxygen content must be less than 12 ppm). Maintain a constant mixed during the compounding process formulation vessel.

Glacial acetic acid is added to the formulation vessel and dissolved completely. Further, sodium acetate is added to the formulation vessel and dissolved completely. The solution is then adjusted to pH 5.2 with 1 N sodium hydroxide or hydrochloric acid. The esmolol HCl drug substance is added to the formulation vessel and dissolved completely.

Both propylene glycol and ethyl alcohol are added to the formulation vessel and dissolved completely. The solution is brought to final volume with water for injection and mixed. The bulk product is filtered through a 0.45 pre-filter and 0.2 μm filter and filled into 250 mL modified flexible plastic container and sealed. The products are then loaded into an autoclaving sterilizer and sterilized at 121° C. for 20 minutes. After cool to ambient conditions, these bags are sealed in aluminum foil overpouches and subjected to stability studies.

Example 2

| Ingredient | Concentration, mg/mL |
|---|---|
| Esmolol | 10-30 mg/mL |
| Sodium Tartrate dihydrate | 0.35-1.80 mg/mL |

-continued

| Ingredient | Concentration, mg/mL |
|---|---|
| Tartaric Acid | 0.025-0.76 mg/mL |
| Ethyl Alcohol, USP | 0.15-0.5% |
| Propylene glycol USP | 0.15-0.5% |
| Water for Injection, USP | Qs |
| Target pH | 5.2 |

Charge the formulation tank with about eighty percent (80%) of the final volume water for Injection while sparging with Nitrogen (dissolved oxygen content must be less than 12 ppm). Maintain a constant mixed during the compounding process formulation vessel.

Glacial acetic acid is added to the formulation vessel and dissolved completely. Further, sodium acetate is added to the formulation vessel and dissolved completely. The solution is then adjusted to pH 5.2 with 1 N sodium hydroxide or hydrochloric acid. The esmolol HCl drug substance is added to the formulation vessel and dissolved completely.

Both propylene glycol and ethyl alcohol are added to the formulation vessel and dissolved completely. The solution is brought to final volume with water for injection and mixed. The bulk product is filtered through a 0.45 pre-filter and 0.2 μm filter and filled into 250 mL modified flexible plastic container and sealed. The products are then loaded into an autoclaving sterilizer and sterilized at 121° C. for 20 minutes. After cool to ambient conditions, these bags are sealed in aluminum foil overpouches and subjected to stability studies.

Example 3

| Ingredient | Concentration, mg/mL |
|---|---|
| Esmolol | 10-30 mg/mL |
| Sodium Tartrate dihydrate | 0.35-1.80 mg/mL |
| Tartaric Acid | 0.025-0.76 mg/mL |
| Ethyl Alcohol, USP | 0.15-1% |
| Glycerin, USP | 0.15-2% |
| Water for Injection, USP | Qs |
| Target pH | 5.2 |

Charge the formulation tank with about eighty percent (80%) of the final volume Water for Injection while sparging with Nitrogen (dissolved oxygen content must be less than 12 ppm). Maintain a constant mixed during the compounding process formulation vessel.

Glacial acetic acid is added to the formulation vessel and dissolved completely. Further, sodium acetate is added to the formulation vessel and dissolved completely. The solution is then adjusted to pH 5.2 with 1 N sodium hydroxide or hydrochloric acid. The Esmolol HCl drug substance is added to the formulation vessel and dissolved completely. Both propylene glycol and ethyl Alcohol are added to the formulation vessel and dissolved completely. The solution is brought to final volume with Water for Injection and mixed. The bulk product is filtered through a 0.45 pre-filter and 0.2 μm filter and filled into 250 mL modified flexible plastic container and sealed. The products are then loaded into an autoclaving sterilizer and sterilized at 121° C. for 20 minutes. After cool to ambient conditions, these bags are sealed in aluminum foil overpouches and subjected to stability studies.

Example 4

| Exemplary specific formulations of the present invention include: | | |
|---|---|---|
| Ingredient | Ex. 4-a | Ex. 4-b |
| Esmolol HCl | 10.0 mg/mL | 20.0 mg/mL |
| Sodium Acetate Trihydrate | 0.68 mg/mL | 0.68 mg/mL |
| Glacial Acetic Acid | 0.30 mg/mL | 0.30 mg/mL |
| Ethanol | 10 mg/mL | 10 mg/mL |
| Propylene Glycol | 10 mg/mL | 10 mg/mL |
| Hydrochloric Acid | As required | As required |
| Sodium Hydroxide | As required | As required |
| Water for Injection | Q.S. (quantity sufficient) | Q.S. (quantity sufficient) |
| Appearance | Clear and Colorless | Clear and Colorless |
| Apparent pH | 4.9 | 4.8 |
| Extractable Volume | 255 mL | 102 mL |

Example 5

The stability studies were performed under 25° C. and 40° C. for flexible containers as mandated by the International Conference on Harmonization (ICH) guidance. At a pre-determined stability intervals, bags of each solution were tested for pH, potency, physical appearance and particulate matter. The concentration of the drug and the related degradation products was determined by a high performance liquid chromatographic (HPLC) method. The data gathered to date for the Esmolol ready-to-use pharmaceutical compositions described herein demonstrates about 5% drop in drug concentration under 25° C. condition for 12 months and about 4.5% formation of impurities. However under accelerated condition (at 40° C.) for 6 months the drug concentration dropped by about 8% with a corresponding decomposition products of about 7.5% Based on published literature by Rosenberg, L. S. et. al., "An accurate Prediction of the pH Change Due to Degradation: Correction for a "Produced" Secondary Buffering System." Pharmaceutical Research 5.8 (1988): 514-517, activation energies for Esmolol decompositions is about 19-21.5 Kcal/mol. Under these conditions (assumption Ea=19 Kcal/mol) from the 40° C. predict to a product shelf life of 24 months expiration at under 25° (see, e.g., Connors, K. A., et al., Chemical Stability of Pharmaceuticals, A Handbook for Pharmacists, John Wiley & Sons, 2d ed. 1986. Typically, when a pharmaceutical compositions can maintained such higher drug concentration at room temperature for at least 12 months, the term "stable formulation", is implied as used herein, means remaining in a state or condition that is suitable for administration to a patient.

The stability results are summarized as follows to affirm the product stability:

Stability of 2.5 g/250 mL bags stored at various temperatures/relative humidity (RH) and times was evaluated using a composition for 10 mg/mL esmolol (2.5 g/250 mL) which contained 1% esmolol (10 mg/mL) plus 1% ethyl alcohol (~10 mg/mL) plus 1% propylene glycol (~10 mg/mL) in sodium acetate buffer.

Stability of 2.5 g/250 mL Bags Stored at Various Temperatures/RH and Times

| Test Time | Percent Remaining | pH | ASL-8123 | Propyl Esters | Ethyl Ester | Visual Inspection | Particulate Matter*** Particles ≥3 mm | Particles ≥25 mm |
|---|---|---|---|---|---|---|---|---|
| 25° C./35% RH* | | | | | | | | |
| Pre autoclaving | 101.2 | 4.9 | 0.03 | <0.03 | <0.03 | CCSFP** | 0 | 0 |
| Initial | 100.31 | 4.9 | 1.30 | <0.03 | <0.03 | CSFP | 0 | 1 |
| 3 months | 100.0 | 4.9 | 2.13 | <0.03 | <0.03 | CSFP | 0 | 1 |
| 6 months | 99.68 | 4.8 | 2.87 | <0.03 | <0.03 | CSFP | 0 | 0 |
| 9 months | 98.43 | 4.8 | 3.72 | <0.03 | <0.03 | CSFP | 1 | 2 |
| 12 months | 96.86 | 4.8 | 4.44 | <0.03 | <0.03 | CSFP | 0 | 2 |
| 40° C./15% RH* | | | | | | | | |
| Pre autoclaving | 101.2 | 4.9 | 0.03 | <0.03 | <0.03 | CSFP | 0 | 0 |
| Initial | 100.31 | 4.9 | 1.30 | <0.03 | <0.03 | CSFP | 0 | 1 |
| 1 months | 99.27 | 4.9 | 2.32 | <0.03 | <0.03 | CSFP | 0 | 2 |
| 2 months | 98.13 | 4.8 | 3.34 | <0.03 | <0.03 | CSFP | 0 | 0 |
| 3 months | 96.23 | 4.8 | 4.36 | <0.03 | 0.03 | CSFP | 1 | 2 |
| 6 months | 93.35 | 4.7 | 7.51 | 0.04 | 0.08 | CSFP | 0 | 1 |

*The storage temperature and humidity conditions.
RH = Relative Humidity
**CCSFP: clear colorless solution free of particles.
***Particulate Matter is measured particles per mL Stability of 2.5 g/250 mL bags stored at various temperatures/relative humidity (RH) and times was evaluated using a composition for 30 mg/mL esmolol (1.5 g/50 mL) which contained 3% esmolol (30 mg/mL) plus 0.1% ethyl alcohol (~1 mg/mL) plus 0.2% glycerin (~2 mg/mL) in sodium tartrate buffer.

Stability of 3.0 g/100 mL Bags Stored at Various Temperatures/RH and Times

| Test Time | Percent Remaining | pH | ASL-8123 | Glycerin Esters | Ethyl Ester | Visual Inspection | Particulate Matter*** Particles ≥600 mm | Particles ≥6000 mm |
|---|---|---|---|---|---|---|---|---|
| 25° C./35% RH* | | | | | | | | |
| Pre autoclaving | 101.2 | 5.1 | 0.15 | <0.03 | <0.03 | CCSFP** | 3 | 100 |
| Initial | 100.31 | 5.0 | 0.80 | <0.03 | <0.03 | CSFP | 1 | 190 |
| 3 months | 100.0 | 5.0 | 1.54 | <0.03 | <0.03 | CSFP | 0 | 80 |
| 6 months | 101.28 | 5.1 | 1.28 | <0.03 | <0.03 | CSFP | 0 | 170 |
| 9 months | 98.43 | 5.0 | 2.32 | <0.03 | <0.03 | CSFP | 3 | 100 |
| 12 months | 96.86 | 4.8 | 3.14 | <0.03 | <0.03 | CSFP | 2 | 12 |
| 40° C./15% RH* | | | | | | | | |
| Pre autoclaving | 101.2 | 5.1 | 0.15 | <0.03 | <0.03 | CSFP | 3 | 10 |
| Initial | 100.31 | 5.0 | 0.80 | <0.03 | <0.03 | CSFP | 1 | 19 |
| 1 months | 99.27 | 4.9 | 1.32 | <0.03 | <0.03 | CSFP | 0 | 11 |
| 2 months | 98.13 | 4.8 | 1.94 | <0.03 | <0.03 | CSFP | 0 | 8 |
| 3 months | 96.23 | 4.7 | 2.56 | <0.03 | 0.03 | CSFP | 3 | 8 |
| 6 months | 93.35 | 4.7 | 5.98 | <0.03 | 0.03 | CSFP | 2 | 14 |

*The storage temperature and humidity conditions.
RH = Relative Humidity
**CCSFP: clear colorless solution.
***Particulate Matter is measured particles per bag

What is claimed is:

1. A co-solvent sterile premixed pharmaceutical product stored in a non-PVC flexible plastic container, wherein said pharmaceutical product has a solution pH between 4.5 and 5.5 and comprises:

a. 5 to 22.5 mg/mL methyl-3-[4-(2-hydroxy-3-isopropylamino)propoxy]phenylpropionate hydrochloride (esmolol hydrochloride), b. a buffering agent to maintain a solution pH between 4.5 and 5.5, c. 0.1% to 3 w/v % of ethyl alcohol, and d. 0.1% to 3 w/v % of one of propylene glycol or glycerin; and wherein said pharmaceutical product is contained in a sealed container and heat-moist sterilized for a period of time sufficient to render the composition sterile.

2. The pharmaceutical product of claim 1, wherein the non-PVC flexible plastic container comprises a 3-7 multilayer, polyolefin based co-extruded film, non-PVC, latex free, plasticizer free, tubing ports are made of a two layer material that is suitable for terminal sterilization.

3. The pharmaceutical product of claim 2, wherein the polyolefin based co-extruded film is selected polypropylene, cycloolefin, polyethylene and copolymerized ethylene vinyl acetate.

4. The pharmaceutical composition of claim 1, wherein the non-PVC flexible plastic container comprises modified tubing ports and closure systems made of a material that is suitable for terminal sterilization.

5. The pharmaceutical product of claim 1, wherein the buffering agent comprises at least one of acetate, tartrate, malate and fumarate.

6. The pharmaceutical product of claim 1, wherein the buffering agent is sodium acetate.

7. The pharmaceutical product of claim 1, wherein the buffering agent is sodium tartrate.

8. The pharmaceutical product of claim 1, wherein the esmolol hydrochloride is contained in an amount ranging from 10 to 30 mg/mL.

9. The pharmaceutical product of claim 1, wherein (d) is propylene glycol.

10. The pharmaceutical product of claim 1, wherein (d) is glycerin.

11. The pharmaceutical product of claim 1, wherein the container is made of a rigid or flexible plastic container and exhibits (i) less than a 2% decrease in the concentration of Esmolol or pharmaceutically acceptable salt thereof after autoclaving (terminal sterilization) and (ii) having formation of related Esmolol esters less than about 0.5% (ii) having co-solvents composition between 0.15% to 5% stored in a non-PVC flexible plastic container and comprising wherein in at least the inner most layer which contacts the esmolol solution comprises a copolymer of ethylene and vinyl acetate.

12. A method of controlling bradycardia and/or controlling hypotension in the diagnosis of cardiac conditions using computerized cardiac tomography in humans comprising administering to a subject in need thereof an effective amount of the pharmaceutical product of claim 1.

13. A method of preparing a pharmaceutical product of claim 1, comprising
preparing a composition comprising:
a. 5 to 22.5 mg/mL methyl-3-[4-(2-hydroxy-3-isopropylamino)propoxy]phenylpropionate hydrochloride (esmolol hydrochloride),
b. a buffering agent to maintain a solution pH between 4.5 and 5.5,
c. 0.1% to 3 w/v % of ethyl alcohol, and
d. 0.1% to 3 w/v % of one of propylene glycol or glycerin;
adding said composition to a non-PVC flexible plastic container;
sealing said container; and
subjecting the sealed container to heat-moist sterilization for a period of time sufficient to render the composition sterile thereby forming said pharmaceutical product.

14. The method of claim 13, wherein said heat-moist sterilization is autoclaving.

15. The method of claim 14, wherein said autoclaving is at a temperature ranging from 110 to 130° C. for a period of time ranging from 7 to 60 minutes.

16. A method of preparing a pharmaceutical product of claim 1, comprising
preparing in a non-PVC flexible plastic container a composition comprising:
a. 5 to 22.5 mg/mL methyl-3-[4-(2-hydroxy-3-isopropylamino)propoxy]phenylpropionate hydrochloride (esmolol hydrochloride),
b. a buffering agent to maintain a solution pH between 4.5 and 5.5,
c. 0.1% to 3 w/v % of ethyl alcohol, and
d. 0.1% to 3 w/v % of one of propylene glycol or glycerin;
sealing said container; and
subjecting the sealed container to heat-moist sterilization for a period of time sufficient to render the composition sterile thereby forming said pharmaceutical product.

17. The method of claim 16, wherein said heat-moist sterilization is autoclaving.

18. The method of claim 17, wherein said autoclaving is at a temperature ranging from 110 to 130° C. for a period of time ranging from 7 to 60 minutes.

* * * * *